(12) United States Patent
McMullen et al.

(10) Patent No.: US 9,971,164 B2
(45) Date of Patent: May 15, 2018

(54) FLUORESCENCE COLLECTION OBJECTIVE OPTICAL SYSTEM AND METHOD

(75) Inventors: Jesse McMullen, Mississauga (CA); Warren Zipfel, Ithaca, NY (US)

(73) Assignee: Cornell University, Ithaca, NY (US)

( * ) Notice: Subject to any disclaimer, the term of this patent is extended or adjusted under 35 U.S.C. 154(b) by 1262 days.

(21) Appl. No.: 13/576,787

(22) PCT Filed: Feb. 8, 2011

(86) PCT No.: PCT/US2011/024023
§ 371 (c)(1),
(2), (4) Date: Aug. 2, 2012

(87) PCT Pub. No.: WO2011/097616
PCT Pub. Date: Aug. 11, 2011

(65) Prior Publication Data
US 2012/0293863 A1  Nov. 22, 2012

Related U.S. Application Data

(60) Provisional application No. 61/302,190, filed on Feb. 8, 2010.

(51) Int. Cl.
*G02B 21/06* (2006.01)
*G02B 27/14* (2006.01)
*G02B 21/02* (2006.01)
*G02B 21/33* (2006.01)
*G01N 21/64* (2006.01)

(52) U.S. Cl.
CPC .......... *G02B 27/145* (2013.01); *G02B 21/02* (2013.01); *G02B 21/33* (2013.01); *G02B 27/141* (2013.01); *G01N 21/6458* (2013.01)

(58) Field of Classification Search
CPC .... G02B 21/02; G02B 27/145; G02B 27/141; G02B 21/33; G02B 21/0024; G02B 21/0076; G02B 21/008; G02B 21/082; G02B 21/365; G02B 26/10; G21N 21/6458; G01N 27/44721
USPC ....... 359/385, 629, 634, 643, 656, 665, 689, 359/659, 368, 658, 355
See application file for complete search history.

(56) References Cited

U.S. PATENT DOCUMENTS

| 6,219,189 B1 * | 4/2001 | Tomimatsu | G02B 21/02 359/355 |
|---|---|---|---|
| 6,717,756 B2 * | 4/2004 | Berman | G02B 26/10 347/233 |
| 7,120,109 B1 * | 10/2006 | Kim | G11B 7/1376 369/112.24 |
| 2001/0008701 A1 * | 7/2001 | Paterson et al. | 428/522 |

(Continued)

*Primary Examiner* — Mustak Choudhury
(74) *Attorney, Agent, or Firm* — Bond, Schoeneck & King, PLLC; William Greener

(57) ABSTRACT

An optical system particularly suited for non-linear fluorescence collecting includes a front lens system, a rear lens system, and a bulk, dichroic beam splitting component intermediate the front lens system and the rear lens system to direct the fluorescent emission from a target object to a photodetector. A lens housing may have a reflective coating on an interior surface thereof. The objective optical system is particularly advantageous for use in cases where large fields of view and high collection efficiencies are desirable.

29 Claims, 7 Drawing Sheets

(56) References Cited

U.S. PATENT DOCUMENTS

| | | | |
|---|---|---|---|
| 2002/0064789 A1* | 5/2002 | Weiss | B82Y 15/00 |
| | | | 435/6.14 |
| 2004/0031930 A1* | 2/2004 | Wolleschensky | G02B 21/0032 |
| | | | 250/458.1 |
| 2004/0165165 A1* | 8/2004 | Yun et al. | 355/53 |
| 2008/0088918 A1* | 4/2008 | O'Connell | G02B 21/365 |
| | | | 359/371 |
| 2008/0212069 A1* | 9/2008 | Goldberg | B01L 3/502761 |
| | | | 356/36 |
| 2008/0277595 A1* | 11/2008 | Lundquist | G01N 27/44721 |
| | | | 250/458.1 |
| 2010/0321786 A1* | 12/2010 | Rahn et al. | 359/634 |
| 2013/0324858 A1* | 12/2013 | Xu et al. | 600/478 |

\* cited by examiner

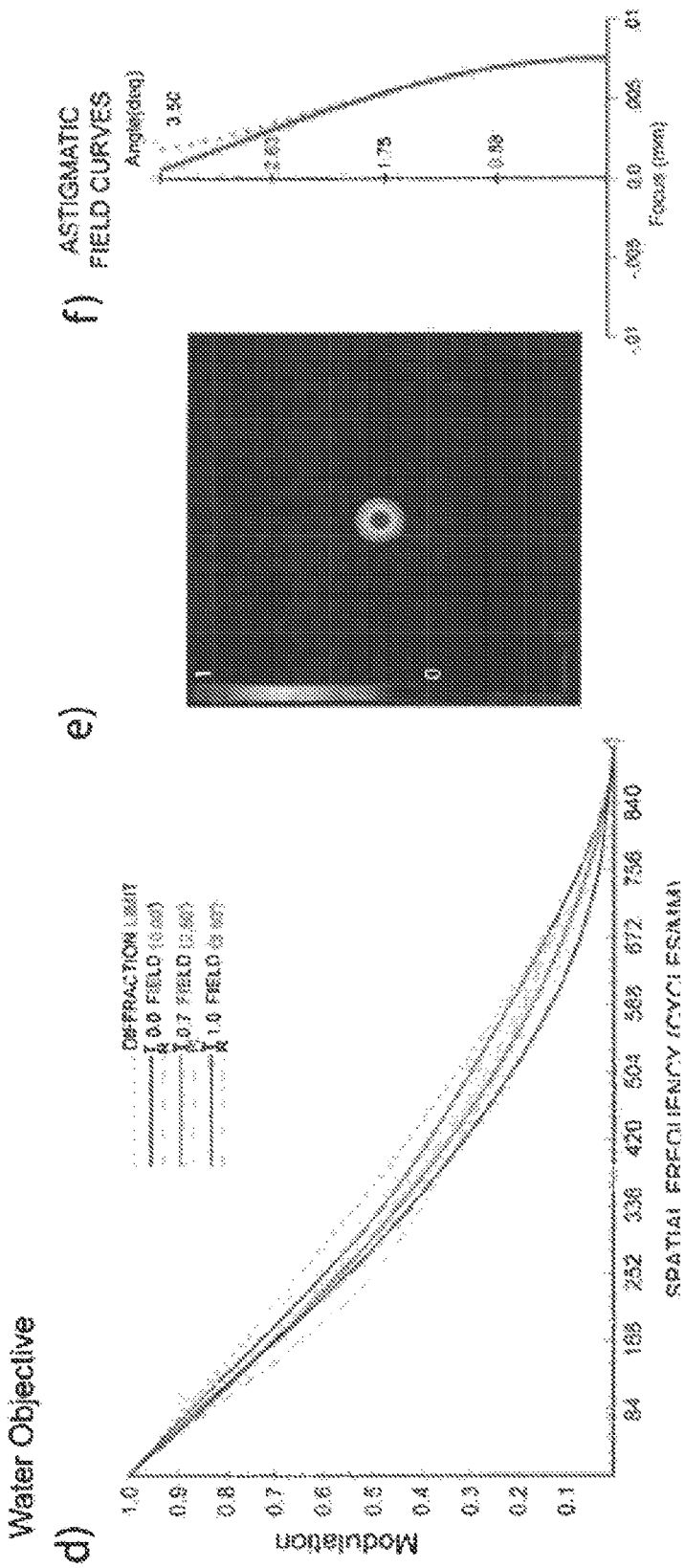
FIG. 2 (con't)

FLUORESCENCE COLLECTION OBJECTIVE OPTICAL SYSTEM AND METHOD

RELATED APPLICATION DATA

The instant application claims priority to International Patent Application No. PCT/US2011/024023 filed on Feb. 8, 2011, which itself claims the benefit of U.S. provisional patent application Ser. No. 61/302,190 filed on Feb. 8, 2010, the subject matter of which is herein incorporated by reference in its entirety.

STATEMENT REGARDING FEDERALLY SPONSORED RESEARCH OR DEVELOPMENT

This invention was made with government support under CA116583 and RR004224 awarded by NIH. The government has certain rights in the invention.

BACKGROUND

Embodiments of the invention are directed to the field of optical systems, particularly to objective lenses and, more particularly to objective lenses for use in fluorescence collection and imaging in multiphoton (MP) and second harmonic generation (SHG) applications including microscopy and endoscopy.

The multiphoton imaging techniques known as multiphoton microscopy (MPM) has developed into a standard tool for the life scientist with far reaching applications ranging from basic cell biology to imaging physiology and disease progression in live animals. This robust form of laser scanning microcopy is ideal for experiments in which cellular and sub-cellular resolution fluorescence imaging is required in a highly scattering medium. As the technique has advanced there has been a corresponding development of new objective lenses specifically for use in multiphoton microscopy. These new designs have increased IR transmission and obtained high numerical apertures (NAs) at relatively low magnification (e.g., Olympus 25×/1.05 NA; Zeiss 20×/1.0 NA). Other collection schemes have been reported, which exploit the principle that all of the collected emission light in MPM—even the scattered photons—contribute to useable signal, have increased the overall solid angle sampled by implementing additional collection optics such as a parabolic reflector underneath the tissue, or a ring of waveguides surrounding it. High NA reflecting objectives that efficiently collect fluorescence have also been demonstrated.

Although high numerical aperture is important to achieve the highest resolution, there are cases in which the experimenter is willing to sacrifice resolution for an increase in the field of view (FOV), for example, in cell tracking experiments in tissues or for observations of calcium oscillations in large neuronal networks. Additionally, a wider field of view would be particularly useful for "multiphoton pathology" applications. Existing technology has been focused on higher numerical aperture objective designs with fields of view under a millimeter. The translation of MPM from the laboratory to the operating room is currently underway with various research groups developing MPM endoscopes capable of performing in-vivo optical biopsies. The direct MPM imaging of fresh unstained biopsy tissue has been demonstrated to provide instant histological grade images without the tedious preparation necessary to produce standard sectioned slides, and may become an indispensable part of clinical practice. In addition, the intrinsic contrast provided both by autofluorescence from endogenous fluorophores such as NADH, flavins and other autofluors, as well as second harmonic generation from such macromolecules as collagen, adds information beyond morphometric parameters. However, some of these signals are weaker than typical dyes by several orders of magnitude, and it is therefore important to maximize the collection optics for this particular application.

In view of the foregoing discussion and the current state of technology represented here, the inventors have recognized a need for new objective lens designs motivated by the requirements of: (1) large field of view; (2) long working distance; (3) a sufficient numerical aperture for reasonable optical sectioning and single cell resolution; (4) collection of as large of a solid angle as possible; (5) an inexpensive design to fabricate; and (6) chromatic correction over at least the bandwidth of a typical femtosecond pulse (10-15 nm), as well as advantageous and beneficial solutions thereto as provided according to embodiments of the invention as disclosed below.

SUMMARY

An embodiment of the invention an objective optical system that includes a front lens system and a rear lens system, aligned along an optical axis, wherein the front lens system is adjacent an object; and a bulk, dichroic beam splitting component disposed along the optical axis intermediate the front lens system and the rear lens system. In an aspect, the bulk, dichroic beam splitting component is in the form of a cube and may, e.g., be in the form of a cylindrical wedge (and may include any necessary focusing optics for a converging or diverging beam or other suitable geometry. In various non-limiting aspects, the system has a scan angle up to 6 degrees, a numerical aperture up to 0.5, and a field of view up to 5 mm; a numerical aperture (NA) equal to or greater than 0.02 and a Strehl ratio greater than 0.800 over a full scan angle up to 7 degrees; a numerical aperture (NA) equal to or greater than 0.02 and a Strehl ratio greater than 0.860 over a full scan angle up to 5.6 degrees. In various non-limiting aspects, the system consists of a refracting lens system, wherein the front lens system consists of a single front lens and the rear lens system consists of two lens elements; the system consists of a refracting lens system, wherein the front lens system consists of a single front lens and the rear lens system consists of three lens elements, wherein the system is a liquid immersion optical system; the system is a water immersion optical system; the refracting lens system consists of spherical and planar refracting surfaces; the front lens has a convex rear surface and a plano-concave front surface, and the rear lens system includes a front lens element having a concave front surface and a convex rear surface and a rear lens element having a convex front surface and a convex front surface. According to an aspect, the system includes a lens system housing (e.g., lens barrel, casing, endoscope housing) having a reflective coating on at least a portion of an interior surface thereof that houses the beam splitting component and the front lens system. Various non-limiting, exemplary applications of the embodied invention include a microscope objective for ex-vivo sample light collection and/or imaging and an objective system for an endoscope for in-vivo sample light collection and/or imaging. The overall optical system can transmit light in an optical output spectrum from about 400 to 1600 nanometers (nm), but the front lens system and beam splitter may be made of a more highly UV transmissive material capable of transmission to about 200 nm.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIG. 5a schematically illustrates the embodied objective optical system in an exemplary single detection channel microscope or laparoscope application; FIG. 5b illustrates a multi-detection channel microscope or laparoscope application.

DETAILED DESCRIPTION OF EXEMPLARY EMBODIMENTS

Figure 1:
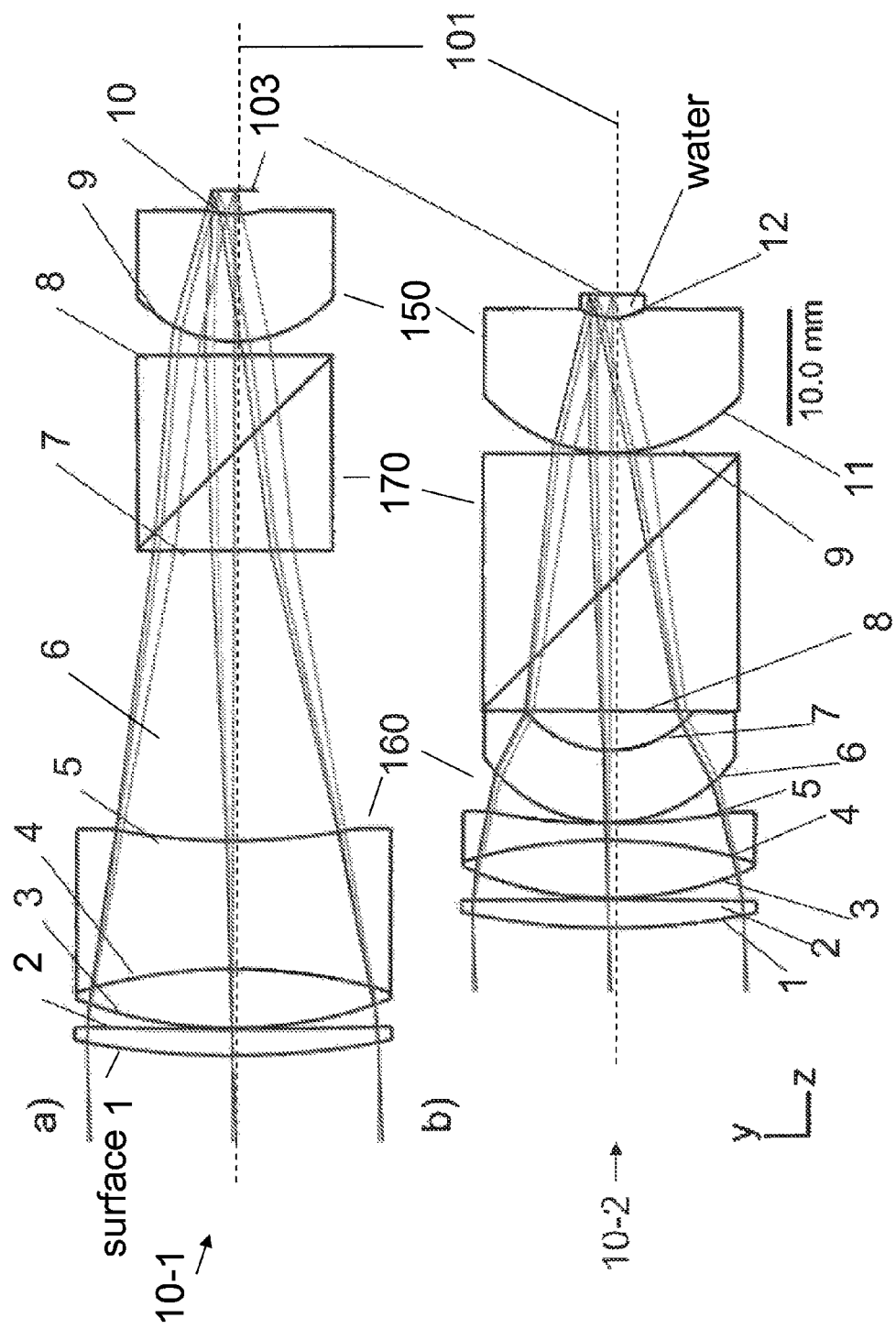
FIG. 1(a, b) are schematic optical layouts of an air-immersion and a water-immersion objective optical system, respectively, according to non-limiting, illustrative aspects of the embodied invention.

An embodiment of the invention is a novel objective optical system 10 for use in non-linear fluorescence (i.e., multi-photon) and harmonic generation (e.g., second harmonic generation (SHG), third harmonic generation, etc) collection and imaging applications (non-limiting e.g.: multi-photon microscopy; endoscopy). The embodied optical system design is characterized by (1) large field of view; (2) long working distance; (3) a sufficient numerical aperture for reasonable optical sectioning and single cell resolution; (4) collection of as large of a solid angle as possible; (5) inexpensive fabrication due to design considerations; and (6) chromatic correction over at least the bandwidth of a typical femtosecond pulse (10-15 nm). The embodied optical system most advantageously includes an internal (to the objective system), bulk, dichroic beam splitting component that can, in an operational example, propagate at least visible light emitted and/or reflected from a target object and reflect fluorescent emission from the target object, which will then be directed to one or more detectors per a desired application. The internal, bulk, dichroic beam splitting component has sufficient optical surface quality as known in the art and provides the system with a minimum number of light-wasting (e.g., scattering, absorbing, etc.) surfaces between the object (e.g., biological sample) and detector(s), while maintaining a reasonable numerical aperture and field of view as parameterized herein.

Exemplary optical design parameters for the embodied invention included an objective field of view (FOV) of at least 4 mm at zoom 1 (i.e., known in the art as corresponding to widest scan angle setting) on our scanning microscopes and up to about 5 mm over a full scan angle of up to 6 degrees, a numerical aperture (NA) up to 0.5, and a working distance of at least 2 mm in a highly scattering medium. Although this is more than twice the imaging penetration depth of a typical or conventional MPM system, a larger working distance becomes advantageous when imaging the irregular surfaces common in tissue and live animal imaging cases. Also, based on the requirements of typical large FOV imaging experiments, we imposed the requirement that the axial FWHM of a two-photon focal volume be no more than 10 microns (μm) maximum, i.e., roughly the thickness of a cell layer. For an objective lens having a NA<0.7, in an immersion medium of refractive index n, the dimensions (and so the sectioning capability) of the two-photon focal volume can be given as:

$$\omega_{x,y}=0.32\lambda/(2)^{1/2}NA, \omega_z=[0.532\lambda/(2)^{1/2}][1/(n-(n^2-NA^2)^{1/2})] \quad (1)$$

where $\omega_{x,y}$ and $\omega_z$ are the lateral and axial 1/e waist of the focal volume for a given wavelength λ. Using these equations, a desired minimum resolution specification was met by an NA of ~0.3 in air and ~0.35 for an objective designed to be immersed in water. The upper limit on objective NA was also set by the size of the lens back aperture. To achieve the optical resolution possible by a given lens numerical aperture, the 1/e diameter of the laser beam at the objective back aperture is on the order the diameter of the entrance pupil, which we set as no more than 25 mm for the diameter of this stop, and which we accommodated in our scanning systems using a scan lens/tube lens combination that produces an ~12× increase in the laser beam diameter to provide a nearly overfilled back aperture. Although this reduces the available scan angle, this lens design achieves a large FOV at relatively small field angles.

To maximize target emission collection by the optical objective, we increased the acceptance solid angle by enlarging the diameter of the front aperture. An infinity corrected fluorescence objective is designed to collimate light originating from its focal plane so that that it can be translated onto a distant image plane and, as a result, the diameter of its front aperture is dictated by its working distance and NA. However, by incorporating a dichroic beam splitting component into the objective itself, we relaxed the need to collimate the light in order to send it to a distant detector. This allowed for an increase in the size of the front aperture of the objective as well as the application of a reflective coating to the interior of the objective housing at least in that region housing the front lens (closest to the target object) and the dichroic beam splitting component, both of which boosted the collected solid angle far in excess of what one skilled in the art would predict based on NA alone. The embodied design thus effectively decouples the excitation and emission paths within the objective lens.

Throughout the design process an effort was made to limit the fabrication cost of the system. In non-limiting, exemplary aspects, the number of refracting lens elements was limited to three for an air-immersion objective system, and to four (with the addition of one additional meniscus lens element to compensate for aberrations) for a water-immersion system. No aspheric surfaces were used, though they could be implemented to further increase the field of view of the system or the NA, as understood by a person skilled in the art. All lenses were made of stock glasses and were selected to minimize fabrication cost. Only two glass types were used in the two non-limiting, exemplary designs (Schott SF2 and Schott NSK16) as further specified in Table 1.

EXAMPLES

An objective lens was designed to deliver excitation light centered at 780 nm with all of the optics having a default ¼ wavelength magnesium fluoride coating. The system was designed to support a bandwidth of greater than 10 nm (775, 780, and 785 nm all being equally weighted during calculations). Although the reference wavelength was 780 nm, the objective performed well throughout the spectral range of a Ti:Sapphire laser source, with only a small relative shift in the focal plane occurring for different excitation wavelengths (e.g. ~35 μm at 880 nm). Although dispersion due to the focusing elements and beam splitter might appear to be problem at first glance, this design is not substantially more dispersive material than other lenses of similar NA and FOV based on total glass thickness. With the current trend of pre-compensation systems being incorporated into commercial Ti:Sapphire lasers (e.g., Spectra Physics DeepSee), it should be possible to deliver transform limited pulses through it.

The ray tracing software Code V (Optical Research Associates, Pasadena, Calif.) was used to design both an air immersion version 10-1 and a water-immersion version 10-2 of the objective optical system as illustrated in FIGS. 1a and 1b, respectively, and as detailed in Table 1. Table 2 summarizes the lens' parameters.

Referring to FIG. 1a, the air immersion objective lens 10-1 has an NA of 0.3 and a full FOV of 4 mm from an input field angle of ±2.8°. Referring to FIG. 1b, the water immersion objective lens 10-2 utilizes an input field angle of ±3.5° to cover its full field of view, but the higher index of refraction of water increases the numerical aperture to 0.35 and slightly decreases the diameter of the back aperture. Both lenses have a working distance of 2 mm to a target object 103.

An emission-splitting plate dichroic placed directly after the front lens was found to severely degrade the point spread function; however, a dichroic coated, beam splitting cylindrical wedge (14-1, 14-2) incorporated into the lens at that point produced no significant degradation after optimization. This emission diverting optic is dimensioned at its face to match the typical diameter of a photomultiplier tube (PMT) photocathode (~20 mm). However, the rays at this point could also be efficiently coupled into a high NA, high transmission light guide, for example, to direct the light to a more distant multichannel detection system.

Figure 2:
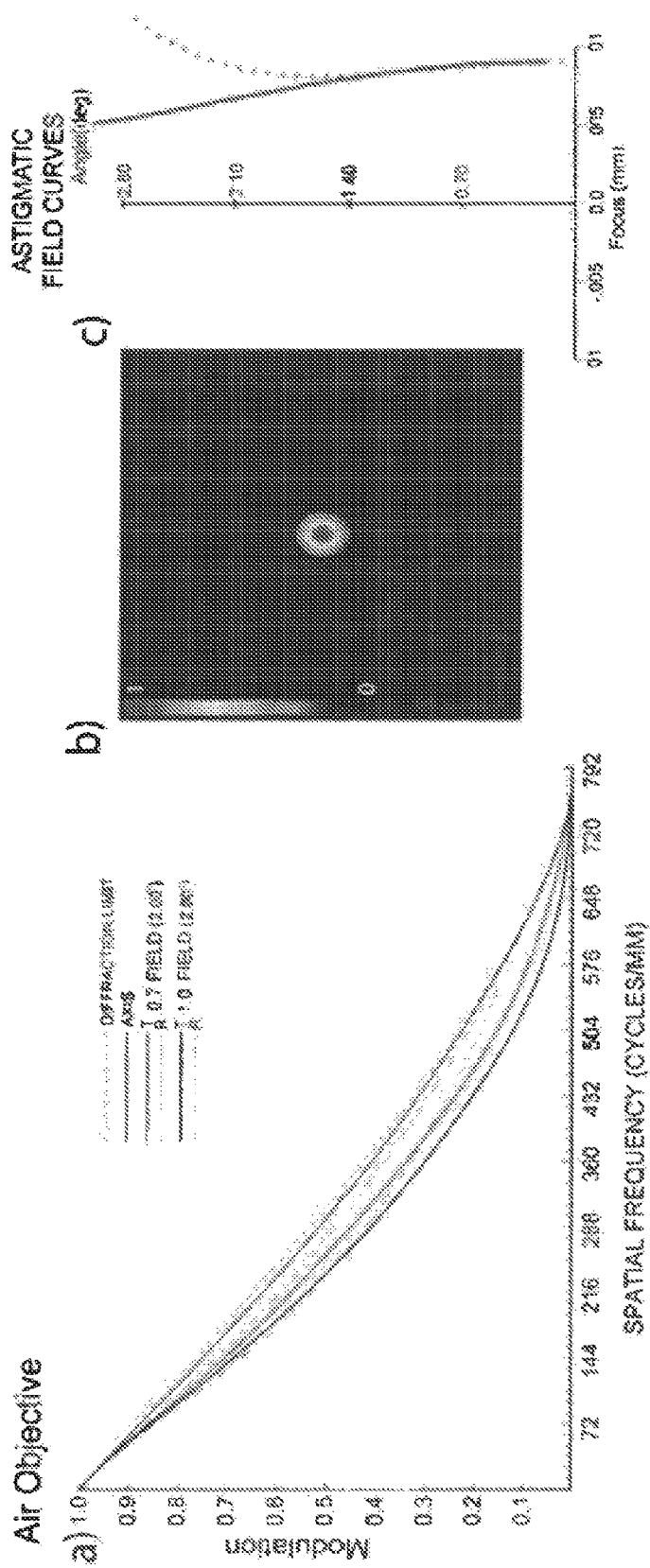
FIG. 2 illustrates the characterization of the excitation transmission for the air- and water-immersion objectives, where (a, d) show modulation transfer functions (MTFs); (b, e) show two photon point spread functions (PSFs) at the greatest field angle (scale bar=2 μm); (c, f) show plots of field curvature at the edge of the field for the tangential (dashed) and sagittal (solid) surfaces, according to illustrative aspects of the invention.

The performance of both of the exemplary lens systems is close to the diffraction limit. The composite Strehl ratio (Table 2), consisting of all three equally weighted wavelengths mentioned above, meets the Marechal criterion for each lens for all three calculated angles, indicating effectively diffraction limited performance across the field. This is confirmed by the modulation transfer functions (MTF) shown in FIG. 2 (a, d) for both designs where the tangential and radial components of each field approximate the diffraction limited curve. The MTFs shown in FIG. 2 were calculated based on the single photon PSFs; the MTFs are further improved using two-photon excitation and the two-photon PSFs at the extreme of the field of view as shown in FIG. 2 (b, e) were found to be effectively diffraction limited. Small amounts of aberration (mainly coma) in the single photon point spread function were minimized by the squar-

TABLE 1

| Air Immersion | | | | Water Immersion | | | |
|---|---|---|---|---|---|---|---|
| Surface # | Y Radius (mm) | Thickness (mm) | Glass | Surface # | Y Radius (mm) | Thickness (mm) | Glass |
| 1 | 68.2985 | 2.2476 | NSK16 | 1 | 58.9079 | 2.4530 | NSK16 |
| 2 | 388.6545 | 0.1000 | | 2 | −679.5758 | 0.1000 | |
| 3 | 37.0318 | 5.0358 | NSK16 | 3 | 30.0456 | 4.9294 | NSK16 |
| 4 | −45.7979 | 10.9444 | SF2 | 4 | −42.4262 | 1.4364 | SF2 |
| 5 | 54.7121 | 24.7277 | | 5 | 55.0440 | 0.1000 | |
| 6 | ∞ | 8.3230 | SF2 | 6 | 13.0909 | 6.1429 | NSK16 |
| 7 | ∞ | 8.3230 | SF2 | 7 | 9.4734 | 3.3587 | |
| 8 | ∞ | 1.2197 | | 8 | ∞ | 10.9560 | SF2 |
| 9 | 11.1877 | 10.8314 | NSK16 | 9 | ∞ | 10.9560 | SF2 |
| 10 | 9.8498 | 2.0000 | | 10 | ∞ | 0.1000 | |
| Image | ∞ | | | 11 | 14.6654 | 11.5217 | SF2 |
| | | | | 12 | 6.0563 | 2.0000 | WATER |
| | | | | Image | ∞ | 0 | |

TABLE 2

| | Entrance pupil (mm) | NA | Field Angle (°) | Focus Position (mm) | Strehl Ratio |
|---|---|---|---|---|---|
| Air Lens | 24.8 | 0.3 | 0 | 0 | 0.963 |
| | | | 2 | 1.43 | 0.971 |
| | | | 2.8 | 2 | 0.869 |
| Water Lens | 23.1 | 0.35 | 0 | 0 | 0.885 |
| | | | 2.5 | 1.43 | 0.868 |
| | | | 3.5 | 2 | 0.812 | ing of the PSF. Finally, the field curvature for both of the lenses, as illustrated in FIG. 2 (c, f) was calculated and found to be within the axial FWHM, with fairly good overlap between the tangential and sagittal rays, indicating minimal astigmatism.

Analysis

Figure 3:
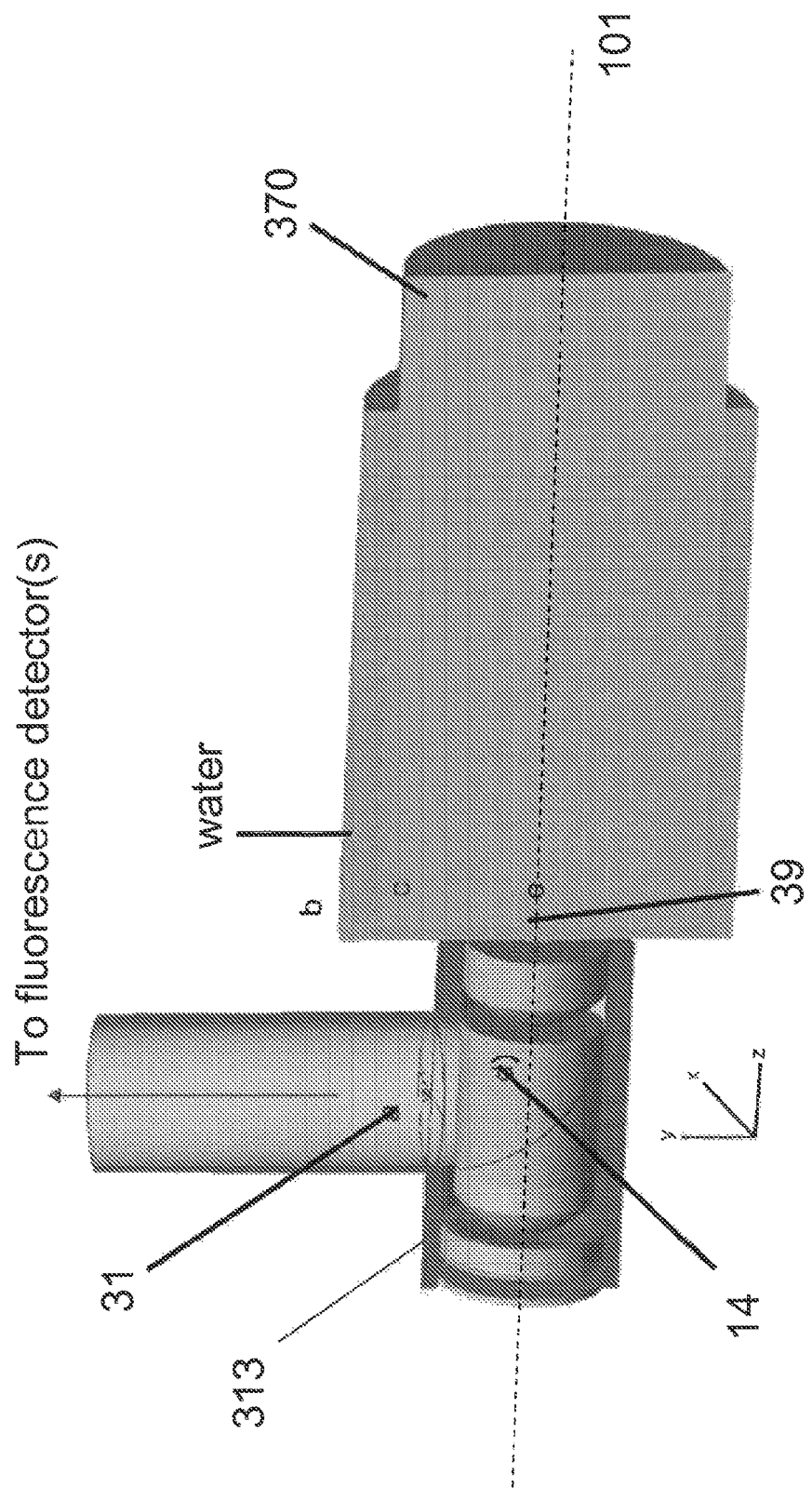
FIG. 3 is a cross sectional LightTools-modeled view of the performance of a water immersion objective (scale bar≈1 cm) in a highly scattering specimen, according to a non-limiting, illustrative aspect of the invention.

To assess the overall collection efficiency of our lens design, we conducted Monte Carlo simulations using the non-sequential ray tracer LightTools (v_6.3 Optical Research Associates, Pasadena, Calif.). This allowed us to calculate the overall "collection numerical aperture" of our lenses, which was different than numerical aperture of the excitation focusing pathway. We compared these designs to the Olympus 4× XLFLUOR, a commercially available macro objective with an NA of 0.28, approximately 1.75× the typical NA of a standard 4×. The lens model we used for our comparison was based on the design shown in the Olympus patent (H. Kazuhiro, Olympus Optical Company, Ltd. "Microscope Objective" Japanese Patent 11-231224 (1999)) and had a slightly smaller NA (0.27) and working distance (28.1 mm) compared to the commercially available Olympus 4× macro objective (NA=0.28 and WD=29.5 mm). Another minor difference in the design shown in the patent was that it was corrected for a sample immersed in 6 mm of water, rather than the 5 mm water layer the commercially available 4× objective is designed around. The three objective lens designs (i.e., the embodied air- and water-immersion designs, and the Olympus 4×) were imported from Code V into LightTools and is illustrated in FIG. 3. An enclosure 313 was placed around the system with an opening for the detector 31, which was placed perpendicular to the optical axis 101 (only one detector was considered for simplicity). In order to collect as many photons as possible, the inner side of the objective enclosure was set to be reflective at and in front of the beam splitter 14, and the lateral edges of the optical components were assumed to be transmitting. In the Olympus 4× objective simulation, a 50.8 mm square dichroic mirror was placed 10 cm along the optical axis away from the back aperture. This was focused into a receiver of 20 mm diameter (the size of our PMT photocathode) by a lens 40 mm wide. This simulation layout represents a typical optimal setup on a standard microscope frame where the focusing nosepiece and other frame parts dictate a ~10 cm minimum spacing. The coatings on both the internal dichroic (our lens models) and the external dichroic (Olympus 4× objective model) were modeled as 100% reflective. In order to assess the effective collection NA ($NA_c$) of the objectives in their respective immersion media (without any scattering), we first examined the collected fraction of photons from an isotropically radiating 587 nm point source 39 located at the intersection of the optical axis and the focal plane. By equating this to the fraction of total solid angle, it was possible to derive the equation for the numerical aperture of collection:

$$NA_c = n \sin(\cos^{-1}(1-2\Phi)) \quad (2)$$

where $\Phi$ is the fraction of the total radiated photons that were incident on the detector. The values of $NA_c$ as displayed in Table 3 were found to be greatly enhanced for the embodied objectives due to the acceptance of the large front aperture and the internal dichroic.

TABLE 3

| Objective | Calculated Numerical Aperture (NA) | Observed Numerical Aperture ($NA_c$) |
|---|---|---|
| Olympus 4× | 0.27 | 0.27 |
| Air Objective | 0.30 | 0.82 |
| Water Objective | 0.35 | 0.98 |

The exemplary objectives and the Olympus 4× objective were also compared for their ability to collect light from a scattering sample. In this case, a cylindrical tissue slab 370 (FIG. 3) 50 mm in diameter and 100 mm long was constructed as a volume scatterer using a Mie scattering model at a wavelength of 587 nm. The scattering mean free path and anisotropy factor g for the tissue were set to 0.05 mm and 0.95 respectively, with a bulk refractive index of the material being 1.33. A small amount of absorption at 587 nm was also included in the model, corresponding to a transmittance per unit length of 0.87—approximating that of human bladder. Light was simulated emitting isotropically from a point source 39 located inside the tissue slab. The number of photons collected was assessed at various points in the focal plane, as well as at various depths within the tissue. For the two embodied, exemplary objectives, $10^5$ photons were simulated, each with a maximum of $10^4$ allowed scattering events. For the Olympus 4× objective, $10^6$ photons were launched to obtain reproducible results, necessitated by the smaller number of rays that reached the detector surface.

Figure 4:
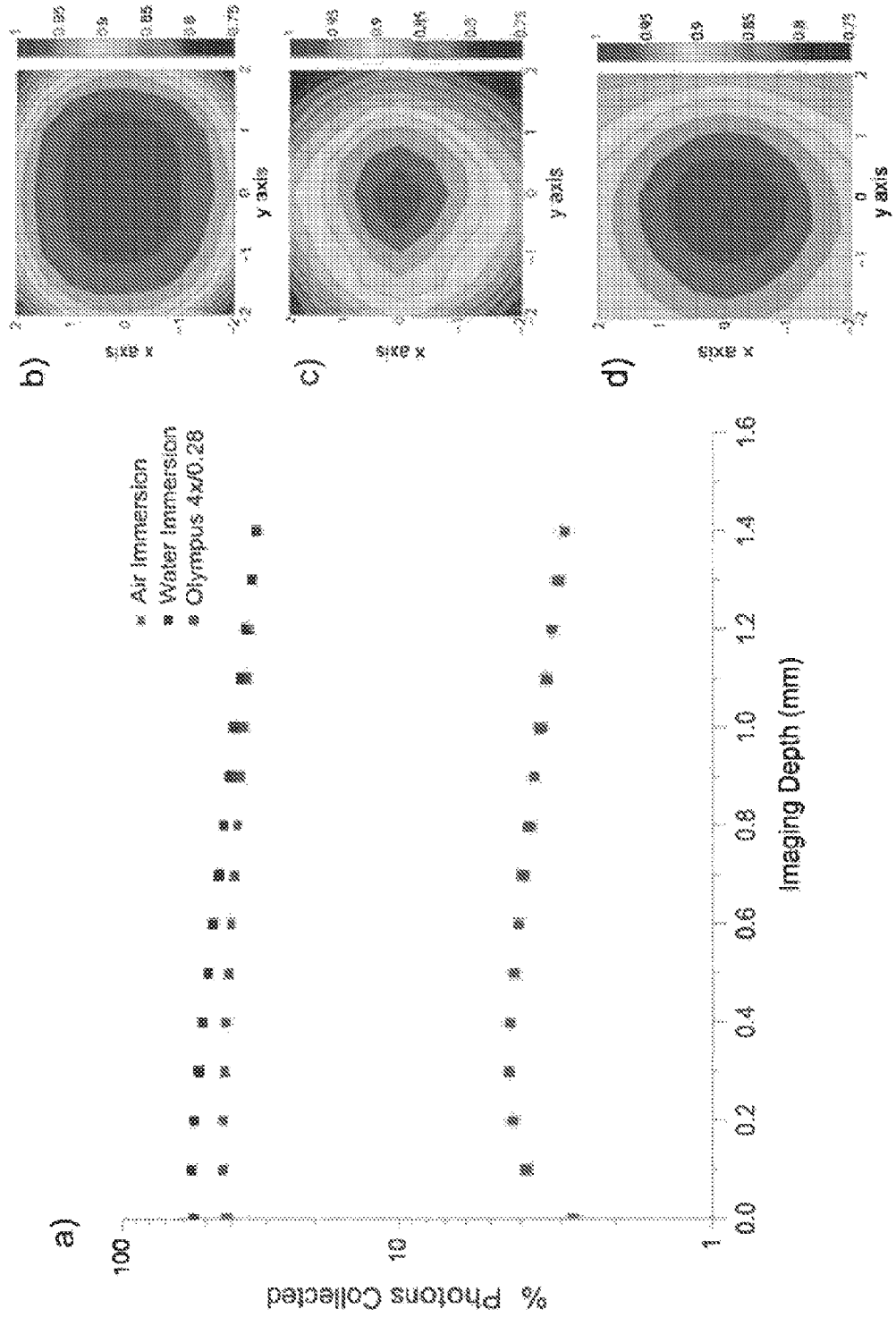
FIG. 4 illustrates simulated light collection in a scattering material, where (a) shows fractional collection as a function of depth of the (on-axis) photon origin in the scattering material; and (b-d) show spatial variance in the collection path. Collection of scattered light calculated for differing photon origin positions over the FOV relative to the optical axis for (b) Olympus 4× objective with focal plane near surface, (c) water immersion objective for focal plane near surface, and (d) the water immersion objective with the focal plane 500 μm into the simulated tissue, according to illustrative aspects of the invention.

The results from these experiments are plotted in FIG. 4a. The embodied objective designs collect roughly an order of magnitude more fluorescence than the Olympus 4× macro lens. The collection of all three objectives was enhanced by scattering from tissue. This occurs in simulation because the depth of the focus is shallow compared to the length of the "tissue," resulting in the bulk of the tissue acting as a minor to photons that had initially been radiated away from the lens but are eventually scattered backwards. This effect is dependent on the particular simulation parameters such as number scattering events allowed, sample absorption, and length of the simulated tissue. The magnitude of this effect has been shown to increase with the field of view of the lens.

Figure 5:
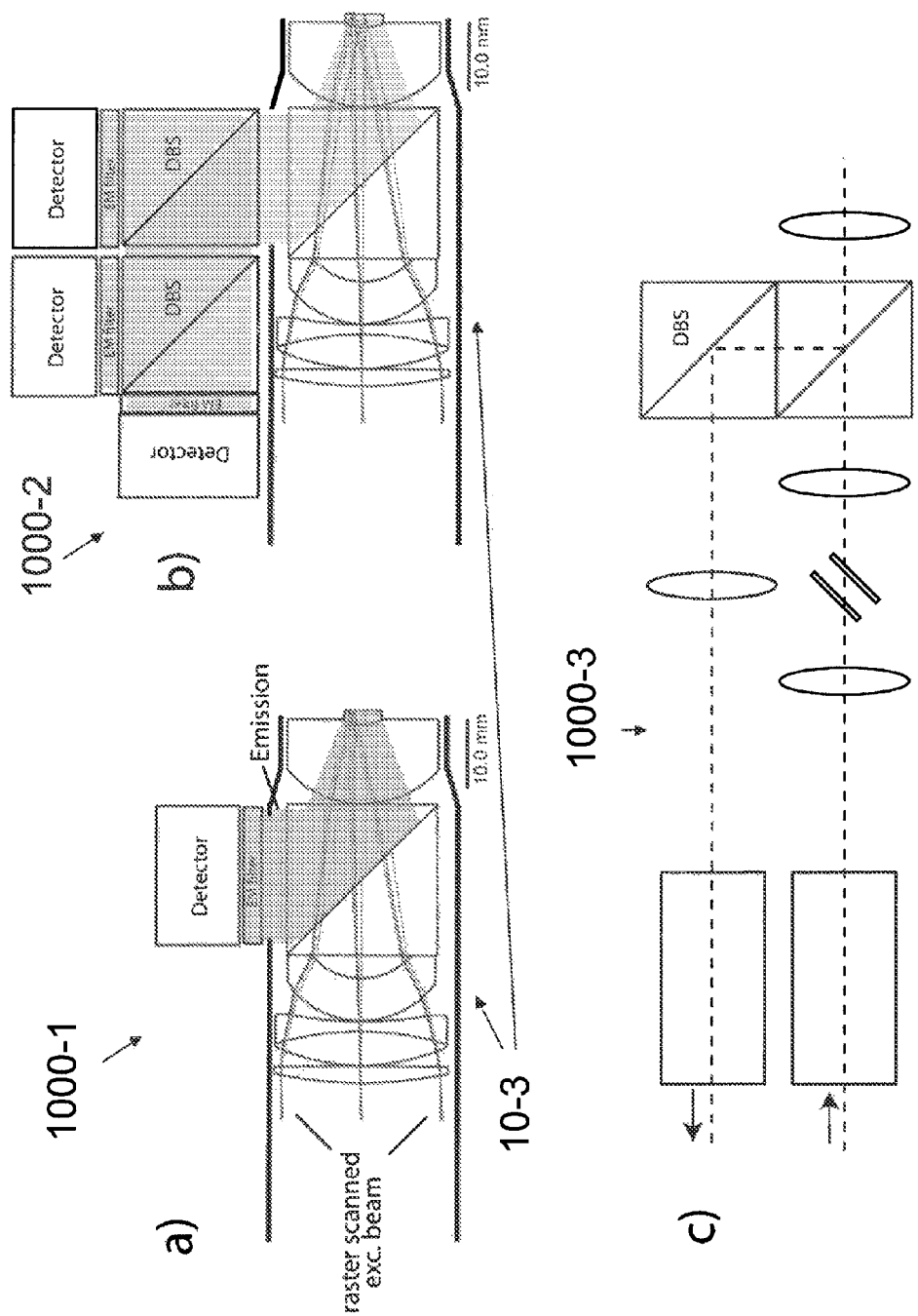
FIG. 5(c, d) illustrate an endoscope application, according to illustrative aspects of the invention.
Figure 5:
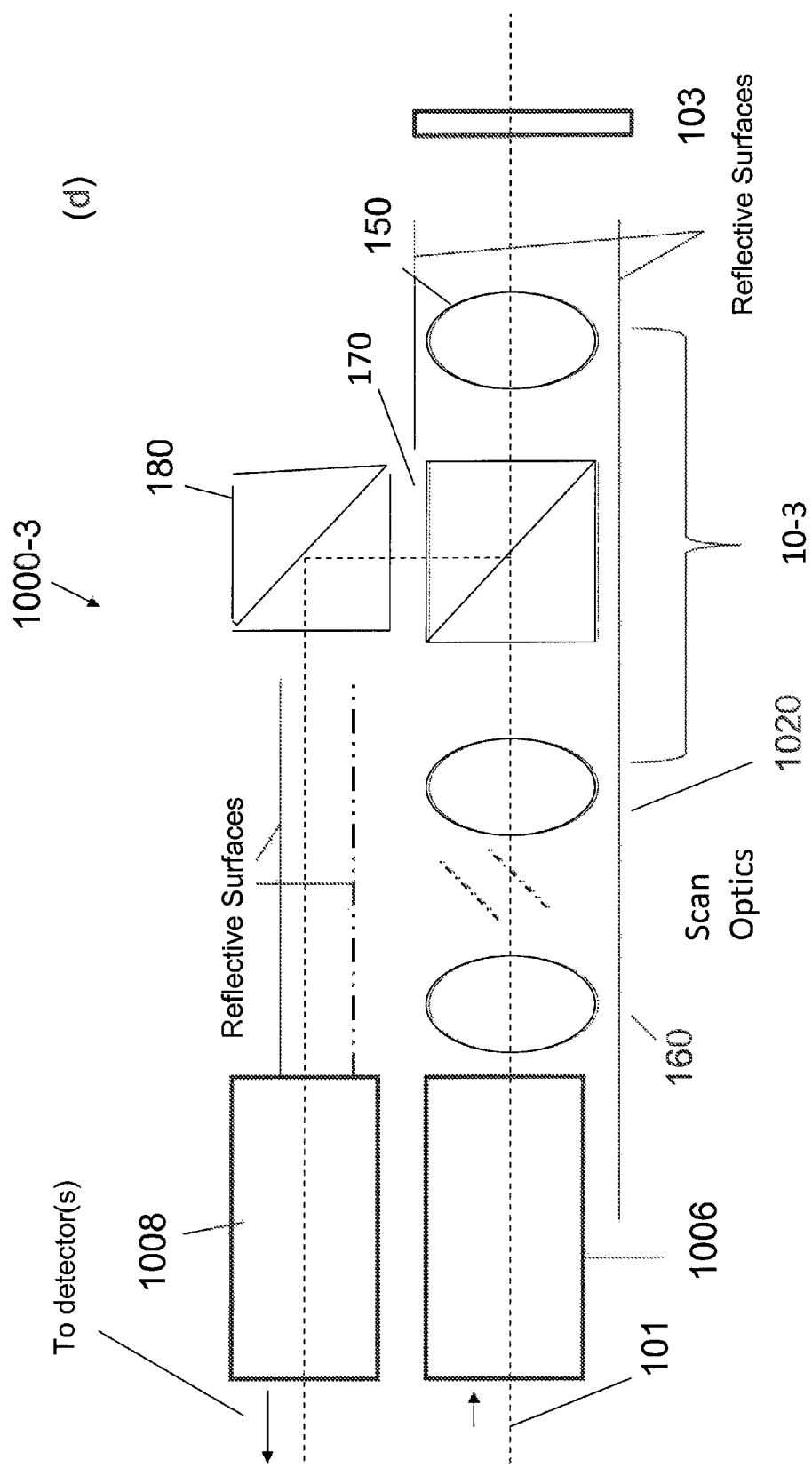

We examined spatial variance in the collection path by moving the point source about the focal plane at half integer intervals between −2 and +2 mm, and tallying the number of rays reaching the receiver at each point. The number of counts, relative to the center of the field of view, was observed to fall off for all three objective designs, although the value was above 75% of the maximum in all cases. However, unlike the Olympus 4× lens (FIG. 4b), which appeared radially symmetric about the optical axis, the incorporation of the dichroic element of the embodied invention created a slight asymmetry in the collection path for both the water-immersion (FIG. 4c) and air-immersion (not shown, but similar to FIG. 4c) objective lens systems. Increased scattering appeared to partially curb this effect for the water immersion lens, which improved substantially even at moderate depths (FIG. 4d), although both the air immersion objective and the Olympus 4× lens showed no change of this ratio with depth. FIG. 5a schematically illustrates the embodied objective optical system in an exemplary single detection channel microscope or laparoscope application 1000-1; FIG. 5b illustrates a multi detection channel microscope or laparoscope application 1000-2; and FIG. 5(c, d) an endoscope application 1000-3 for, e.g., in-vivo observation as distinguished from the exemplary microscopic ex-vivo observation application described herein above. Similar to the objective optical systems 10-1, 10-2 illustrated in FIG. 1, the objective optical system 10-3 includes (referring to FIG. 5(d)) a front lens system 150 and a rear lens system 160 aligned along the optical axis 101, wherein the front lens system is adjacent an object 103 and, a bulk, dichroic beam splitting component 170 having substantially flat entrance and exit surfaces and disposed along the optical axis intermediate the front lens system 150 and the rear lens system 160. As mentioned above, internally incorporating a bulk dichroic beam splitter 170 immediately optically upstream of the front lens system 150 minimizes the number of optical surfaces between that light from the sample 103 must interact with between the sample 103 and the detector(s) (not shown). In the instant aspect, excitation light is delivered to the sample 103 via excitation fiber 1006. Light emitted (scattered, reflected, generated) from the sample propagates through the front lens system 150 and the non-linear fluorescence is reflected by the dichroic beam splitter 170 and directed via component 180 to collection fiber 1008 and to the detector(s). As further illustrated in FIG. 5, the endoscope has a housing 1020 (akin to lens barrel or casing in the microscope aspect) that may advantageously have a reflective coating on at least a portion of an inside surface thereof as shown to increase the amount of light to the detector(s).

The embodied objective optical system demonstrates a novel design for non-linear fluorescence collecting objective lenses, which are particularly advantageous for use in cases where large fields of view and high collection efficiencies are desirable. The exemplary objective lens designs provide a 4 mm large field of view, a moderately low, but useable focusing NA with an effective collection NA approaching 1. The designs were demonstrated to be highly efficient at collecting fluorescence, especially in the scattering samples typical of multiphoton microscopy. The incorporation of such an objective/detector system on an existing microscope should have immediate impact in experiments such as studies of neuronal network signaling, imaging cell migration in tissues explants and live animals, characterization of engineered tissue constructs, and promising new areas such as "instant pathology" based on rapid multiphoton imaging of biopsy samples.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed. No language in the specification should be construed as indicating any non-claimed element as essential to the practice of the invention.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. An objective lens assembly for use in an optical emission collection system that includes a fluorescence-excitation light source and an object from which an optical emission is to be collected, comprising:

a front lens system, a rear lens system, and a bulk, dichroic beam splitting component disposed intermediate the front lens system and the rear lens system and immediately adjacent the front lens system, aligned along a common optical axis, wherein the front lens system is operationally disposed adjacent the object from which the optical emission is to be collected, wherein the rear lens system is operationally disposed such that the objective lens assembly decouples the excitation and emission paths within the objective lens, and wherein the system has a numerical aperture (NA) of focus equal to or greater than 0.02 and a Strehl ratio greater than 0.800 over a full scan angle up to 7 degrees.

2. The objective lens assembly of claim 1, wherein the bulk, dichroic beam splitting component is in the form of a cube.

3. The objective lens assembly of claim 1, wherein the system has an entrance pupil diameter equal to or less than 25 millimeters (mm).

4. The objective lens assembly of claim 1, wherein the system has a numerical aperture (NA) of focus equal to or greater than 0.02 and a Strehl ratio greater than 0.860 over a full scan angle up to 5.6 degrees.

5. The objective lens assembly of claim 1, wherein the system has a field of view (FOV) equal to or greater than about 4 mm.

6. The objective lens assembly of claim 1, consisting of a refracting lens system, wherein the front lens system consists of a single front lens and the rear lens system consists of two lens elements.

7. The objective lens assembly of claim 6, wherein the refracting lens system consists of spherical and planar refracting surfaces.

8. The objective lens assembly of claim 6, wherein the front lens has a convex rear surface and a plano-concave front surface, and the rear lens system includes a front lens element having a concave front surface and a convex rear surface and a rear lens element having a convex front surface and a convex rear surface.

9. The objective lens assembly of claim 6, characterized by a scan angle up to 6 degrees, a numerical aperture up to 0.5, and a field of view up to 5 mm.

10. The objective lens assembly of claim 1, consisting of a refracting lens system, wherein the front lens system consists of a single front lens and the rear lens system consists of three lens elements, wherein the system is a liquid immersion optical system.

11. The objective lens assembly of claim 10, wherein the system is a water immersion optical system.

12. The objective lens assembly of claim 10, wherein the refracting lens system consists of spherical and planar refracting surfaces.

13. The objective lens assembly of claim 10, wherein the front lens has a convex rear surface and a plano-concave front surface, and the rear lens system includes a front lens element having a convex rear surface and a concave front surface, an intermediate lens element having a convex rear surface and a concave front surface, and a rear lens element having a convex rear surface and a concave front surface.

14. The objective lens assembly of claim 10, characterized by a scan angle up to 6 degrees, a numerical aperture up to 0.5, and a field of view up to 5 mm.

15. The objective lens assembly of claim 1, further comprising a lens system housing having a reflective coating on at least a portion of an interior surface thereof that houses the beam splitting component and the front lens system.

16. The objective lens assembly of claim 1, wherein the front lens system and the beam splitting component can transmit light in an optical spectrum from about 200 to 1600 nanometers (nm).

17. An objective lens assembly for use in an optical emission collection system that includes a fluorescence-excitation light source and an object from which an optical emission is to be collected, comprising:

a front lens system, a rear lens system, and a bulk, dichroic beam splitting component disposed intermediate the front lens system and the rear lens system and immediately adjacent the front lens system, aligned along a common optical axis, wherein the front lens system is operationally disposed adjacent the object from which the optical emission is to be collected, wherein the rear lens system is operationally disposed such that the objective lens assembly decouples the excitation and emission paths within the objective lens, further wherein the objective optical system has a numerical aperture (NA) of focus equal to or greater than 0.02 and a Strehl ratio greater than 0.800 over a full scan angle up to 7 degrees, and a field of view (FOV) equal to or greater than about 4 mm.

18. The objective lens assembly of claim 17, wherein the front lens system and the beam splitting component can transmit light in an optical spectrum from about 200 to 1600 nanometers (nm).

19. The objective lens assembly of claim 17, wherein the bulk, dichroic beam splitting component is in the form of a cube.

20. The objective lens assembly of claim 17, wherein the system has an entrance pupil diameter equal to or less than 25 millimeters (mm).

21. The objective lens assembly of claim 17, wherein the system has a numerical aperture (NA) of focus equal to or greater than 0.02 and a Strehl ratio greater than 0.860 over a full scan angle up to 5.6 degrees.

22. The objective lens assembly of claim 17, consisting of a refracting lens system, wherein the front lens system consists of a single front lens and the rear lens system consists of two lens elements.

23. The objective lens assembly of claim 22, wherein the refracting lens system consists of spherical and planar refracting surfaces.

24. The objective lens assembly of claim 22, wherein the front lens has a convex rear surface and a plano-concave front surface, and the rear lens system includes a front lens element having a concave front surface and a convex rear surface and a rear lens element having a convex front surface and a convex rear surface.

25. The objective lens assembly of claim 17, consisting of a refracting lens system, wherein the front lens system consists of a single front lens and the rear lens system consists of three lens elements, wherein the system is a liquid immersion optical system.

26. The objective lens assembly of claim 25, wherein the system is a water immersion optical system.

27. The objective lens assembly of claim 25, wherein the refracting lens system consists of spherical and planar refracting surfaces.

28. The objective lens assembly of claim 25, wherein the front lens has a convex rear surface and a plano-concave front surface, and the rear lens system includes a front lens element having a convex rear surface and a concave front surface, an intermediate lens element having a convex rear surface and a concave front surface, and a rear lens element having a convex rear surface and a concave front surface.

29. The objective lens assembly of claim 17, further comprising a lens system housing having a reflective coating on at least a portion of an interior surface thereof that houses the beam splitting component and the front lens system.

* * * * *